United States Patent [19]

Andersen et al.

[11] 4,020,185
[45] Apr. 26, 1977

[54] STARTER CULTURE MEDIA CONTAINING WHEY

[75] Inventors: Delmar Lloyd Andersen, Syracuse; Louis Russell Boston, Chiitenanga; William H. Seleen, De Witt, all of N.Y.

[73] Assignee: Borden, Inc., Columbus, Ohio

[22] Filed: Apr. 29, 1974

[21] Appl. No.: 464,758

Related U.S. Application Data

[62] Division of Ser. No. 259,862, June 5, 1972, Pat. No. 3,852,158.

[52] U.S. Cl. .................................. 426/36; 195/96; 195/100; 426/41; 426/43; 426/61
[51] Int. Cl.² .................. A23C 19/02; A23C 21/00
[58] Field of Search ............... 195/96, 100; 426/43, 426/41, 61, 185, 239, 36, 37, 582, 583

[56] References Cited

UNITED STATES PATENTS

| | | | |
|---|---|---|---|
| 2,805,950 | 9/1957 | Erekson | 426/41 X |
| 3,048,490 | 8/1962 | Lundstedt | 426/43 X |
| 3,354,049 | 11/1967 | Christensen | 195/100 |
| 3,447,930 | 6/1969 | Francis | 426/239 |

OTHER PUBLICATIONS

Webb, et al., By products from Milk, The Avi Publishing Co., Inc., Westport Conn. 2nd ed. 1970 (pp. 43–45).
Hammer, et al., Bacteriology of Butter Cultures. J. Da. Sci., vol. 26, No. 2. 1943 (pp. 92–97 & 136–138).

*Primary Examiner*—David M. Naff
*Attorney, Agent, or Firm*—George P. Maskas; George A. Kap; Daniel D. Mast

[57] ABSTRACT

Starter cultures for cheese production are prepared using culture media containing on a 100 parts dry basis 0.1 to 30 parts of a nitrogen source, 1–30 parts of a nitrogen source, 1–30 parts of a citrate source and a milk product being the remainder which is selected from the group consisting of undecalcified sweet whey or a major amount of undecalcified sweet whey and a minor amount of nonfat dry milk. The media results in a high and uniform bacteria count, and starter cultures produced therefrom produce cheese that cures fast and has enhanced flavor.

6 Claims, No Drawings

STARTER CULTURE MEDIA CONTAINING WHEY

This is a division, of application Ser. No. 259,862 filed June 5, 1972, now U.S. Pat. No. 3,852,158.

BACKGROUND OF THE INVENTION

The use of a culture media containing a relatively large amount of added citrate result in a higher and more uniform bacteria count in a starter culture. Cheese made using such a starter culture cures faster and has an enhanced flavor.

Citrates have been added to various culture media such as those containing decalcified milk products or enhanced levels of simple sugars, to encourage bacterial growth. U.S. Pat. No. 3,086,866 of Humphreys, et al. and U.S. Pat. No. 3,192,124 of Kheshgi exemplify the prior art in this area. Citric acid has also been added to a culture media to generate a pleasant tasting component which is subsequently added to a cheese product. The prior art in this area is exemplified by U.S. Pat. No. 2,971,847 of Babel. Generally speaking the prior art has resulted in a slower than desired growth of viable bacteria and erratic viable bacterial count after the initial growth period.

SUMMARY

The present invention is based upon a culture media containing added citrate and which does not require decalcified milk or the addition of simple sugars or internally generated carbohydrates. In addition the culture medium of the present invention results in fast growth of bacteria, and retention of high viable bacterial populations throughout the incubation period.

DESCRIPTION OF THE PREFERRED EMBODIMENTS

The culture media of the present invention based upon 100 parts of ingredient consists essentially of:
a. from 10 to 99 parts of a milk product selected from the group consisting of sweet whey, non-fat dry milk, sour whey powder, buttermilk powder, whole milk powder, and mixtures thereof. The milk product is undecalcified and contains at least one part of calcium per thousand parts of milk product. The culture media also contains:
b. from about 0.1 to about 30 parts of a nitrogen source;
c. from about 1 to about 30 parts, based upon citrate anion exclusive of cation weight, of an added citrate source selected from the group consisting of citric acid and salts of citric acid.

The salts are preferably the ammonium or alkali metal salts of citric acid such as sodium or potassium salts, but may also be other water soluble non-toxic salts of citric acid. It is preferable that the milk product be present in an amount from about 70 to 95 parts. The above composition provides higher bacterial counts than prior art starter culture media compositions and also provides a greater uniformity of bacterial counts. The result is that the starter cultures produced using the culture medium can be used sooner than the prior art systems with more favorable results or later than the prior art systems with more favorable results than heretofore known.

Another advantage of the present system is that sweet whey can be used as the milk product, and bacterial counts, higher than those normally obtained with the non-fat dry milk of prior art systems, can be achieved. It is preferred that the major component of the milk product be sweet whey and that a minor component of the product be non-fat dry milk.

The nitrogen source is selected from the group consisting of yeast extract, yeast autolysate, solubilized yeast, food yeast, amino acids, proteins and mixtures thereof. There are many yeast products commercially available. The yeast products and the companies which supply them commercially are as follows: Ardimine YEP, Yeast Products, Inc., 455 Fifth Ave., Paterson, N.J.; Lake States Torula Yeast, St. Regis Paper, Rhinelander, Wisc.; Yeast Autolysate, Universal Foods, 433 E. Michigan St., Milwaukee, Wisc. 55039; and Yeatex, Calvert Vavasseur and Co., Inc., 19 Reactor St., New York, N.Y.; Yeast Autolysate, Ambler Labs, Juneau, Wisc. 53039; and Maggi Standard Light Powder, Nestle Co., White Plains, N.Y.

The yeast product or other nitrogen source preferably is present in an amount of from 0.5 to 10.0 parts.

It is preferable that the citrate source be present in an amount of from about 10 to 20 parts. At the 20 part level good phage inhibition is taking place. The preferable citrates are the ammonium citrate, sodium citrate, potassium citrate and citric acid. Sodium citrate is the most readily commercially available form and provides good buffering activity. The production of high quantities of lactic acid in the starter culture and the maintaining of a good bacterial flora is related to the buffering capability of the citrate present. Sodium citrate has proven itself to be useful in this regard.

For storage, transportation and for the purpose of maintaining the medium in a stable condition, it is preferred that the mixture be in a dry state. The procedure for preparing culture medium is well known in the art and will not be described in detail here.

The bacteria used are those normally used in starter cultures in the manufacture of cheese in an effective amount to cause growth of the bacteria to flourish, but not exceeding 10 parts such bacteria include: Streptococcus cremoris, Streptococcus lactis, Streptococcus citrovorous, Streptococcus paracitrovorus, Streptococcus thermophilus, Streptococcus durans, Streptococcus diacetilactis, Streptococcus faecalis, Lactobacillus acidophilus, Lactobacillus bulgaricus, Lactobacillus brevis, leuconostoc eitrovorum Lactobacillus delbrueckii, Lactobacillus fermenti, Lactobacillus elveticus, Lactobacillus lactis, Lactobacillus plantarum, Lactobacillus thermophilus, Leuconostoc mesenteroides, and Propionibacterium species, and mixtures thereof.

The bacteria which are normally used in cheese manufacture, which are preferable here are Streptococcus cremoris, Streptococcus lactis, Streptococcus citrovorus, Propionibacterium shermanii and mixtures thereof.

The starter culture which has been prepared is used in much the same way as conventional starter cultures have been used in the past. Amount of the starter culture may vary from 0.1 to 5 parts, preferably from 0.5 to 1 part per 100 parts of milk. In preparing the starter culture, from 1 to 20 parts of the culture medium is dispersed in 80–99 parts of water and an effective amount of a bacteria is added to the dispersion. One noticeable difference is that less of the present starter culture is necessary than prior art starter cultures. For example, it is recommended that 0.75 part of the present starter culture be added to 100 parts of milk. Conventionally, one part was required. Other noticeable differences are that the present starter culture can be used sooner than, or later than, conventional starter cultures with far less adverse results than one normally encounters using the prior art starter cultures.

In the following examples, as elsewhere in the specification and claims, all parts are by weight unless specifically expressed otherwise. Acidity is developed titratable acidity expressed as % lactic acid.

EXAMPLE 1

A culture media was prepared by dry blending the following ingredients:
- 69 parts of sweet whey
- 16 parts of non-fat dry milk
- 1 part of yeast extract
- 14 parts of sodium citrate To 89 parts of water at 110° F were added 11 parts of the dry culture medium. Heating was continued to pasteurize the mix and in combination with agitation, to aid in proper mixing. After the dry mix was dissolved, the solution was then heated to 185° F and held at that temperature for 40 minutes. The solution was then rapidly cooled to 70° F. The solution was then inoculated with a mother culture of *Streptococcus lactis* and *Streptococcus cremoris*. The ratio of mother culture to solution was 0.75 part of mother culture per 100 parts of solution. The cultured solution was incubated at 72° F to produce a starter culture.

For comparison purposes a second starter culture was prepared in exactly the same manner except that 11 parts of dry non-fat milk were used as the culture media and added to 89 parts of water.

Over a 24 hour period, measurements were made of lactic acid produced, the number of live bacteria present per cc and pH. The sodium citrate containing starter culture provided a superior buffered system, higher lactic acid production and higher bacteria counts over the 24 hour period than the starter culture employing non-fat dry milk.

Cheddar and Colby cheeses were made using 1 part of the above described starter culture, which had been incubated for 16 hours, per 100 parts of milk. The cheeses made using the sodium citrate containing starter culture cured in less time than the cheeses made using a starter culture based upon non-fat dry milk.

EXAMPLE 2

A starter culture was prepared in the same manner as set forth in Example 1 except that the dry mix contained
- 6 parts of sodium citrate
- 24 parts of non-fat dry milk
- 1 part yeast extract
- 69 parts of sweet whey The acidity of the starter culture at the end of 8 hours of incubation ws 0.42. A starter culture prepared in the same way except that dry non-fat milk was used instead of the dry mix, at the same time had 0.3. This example indicates how much faster acid is produced using the citrate containing media as compared to a conventional media.

EXAMPLE 3

A starter culture was prepared in the same manner as set forth in Example 1 except that the dry mix contained
- 10 parts of sodium citrate
- 1 part yeast extract
- 23 parts non-fat dry milk
- 66 parts sweet whey The acidity of the starter culture produced at the end of the 8 hour incubation period was 0.49. Similar enhanced results were obtained using 14, 17 and 20 part citrate mixes containing one and 2 parts of yeast.

EXAMPLES 4 – 10

The following examples, 4 through 10, set forth the enhanced capability of the citrate containing starter cultures to produce lactic acid. The starter cultures were produced by the same method set forth in Example 1.

EXAMPLE 4

| Composition | % Lactic acid produced at the end of 24 hours |
|---|---|
| 10 parts sodium citrate<br>1 part yeast extract<br>23 parts non-fat dry milk<br>66 parts sweet whey | 0.76 |
| non-fat dry milk | 0.64 |

| Example | Composition | % Lactic acid produced at 16 hours |
|---|---|---|
| 5 | 14 parts sodium citrate<br>1 part yeast extract<br>16 parts non-fat dry milk<br>69 parts sweet whey | 0.76 |
| 6 | 14 parts sodium citrate<br>2 parts yeast extract<br>15 parts non-fat dry milk<br>69 parts sweet whey | 0.80 |
| 7 | 17 parts sodium citrate<br>1 part yeast extract<br>12 parts non-fat dry milk<br>70 parts sweet whey | 0.78 |
| 8 | 17 parts sodium citrate<br>2 parts yeast extract<br>12 parts non-fat dry milk<br>69 parts sweet whey | 0.88 |
| 9 | 20 parts sodium citrate<br>1 part yeast extract<br>10 parts non-fat dry milk<br>69 parts sweet whey | 0.83 |
| 10 | 20 parts sodium citrate<br>2 parts yeast extract<br>9 parts non-fat dry milk<br>69 parts sweet whey | 0.94 |

EXAMPLES 11 – 14

The following table sets forth the enhanced capability of the citrate containing starter culture to produce high bacterial counts. The starter cultures were produced by the same method set forth in Example 1.

| Example | Composition | Bacterial count in live cells/cc |
|---|---|---|
| 11 | 10 parts sodium citrate<br>1 part yeast extract<br>23 parts non-fat dry milk<br>66 parts sweet whey | 330×10⁶ at 16 hours incubation |
| 12 | Comparitive Example using dry non-fat milk solids | 107×10⁶ at 16 hours incubation |
| 13 | 17 parts sodium citrate<br>2 parts of yeast extract<br>12 parts non-fat dry milk<br>69 parts sweet whey | from 10 to 16 hours the count remained above one billion |
| 14 | 20 parts of sodium citrate<br>2 parts of yeast extract<br>9 parts non-fat dry milk<br>69 parts sweet whey | from 10 to 16 hours the count remained above one billion |

EXAMPLES 15 – 10

Both Cheddar and Colby cheeses were each made employing 0.75 parts of starter cultures per 100 parts of milk. The starter cultures were prepared from the following ingredients using the procedure of Example 1. The cheeses produced are recited as follows:

| Examle | Composition | Results |
|---|---|---|
| 15 | 69 parts sweet whey<br>24 parts non-fat dry milk<br>6 parts sodium citrate<br>1 part yeast extract | Fair to good |
| 16 | 66 parts sweet whey<br>23 parts non-fat dry milk<br>1 part yeast extract<br>10 parts sodium citrate | Good |
| 17 | 69 parts sweet whey<br>15 parts non-fat dry milk<br>2 parts yeast extract<br>14 parts sodium citrate | Best |
| 18 | 69 parts sweet whey<br>12 parts non-fat dry milk<br>2 parts yeast extract<br>17 parts sodium citrate | Best |
| 19 | 69 parts sweet whey<br>9 parts non-fat dry milk<br>2 parts yeast extract<br>20 parts sodium citrate | Best |

From the above Examples 15 – 19, it can be seen that the best results are obtained when at least 10 parts of citrate are employed. It can also be seen that higher quantities yest extract favorably effect the quality of the starter culture and its applicability to the cheese making process.

We claim:

1. Process for preparing cheese from milk comprising adding to the milk an effective amount of a starter culture to coagulate the milk by fermentation, the starter culture is prepared from ingredients consisting essentially of A, B, and C in amounts specified below, or about 100 parts basis, by making a solution of ingredients A and B and then inoculating the solution with ingredient C and incubating the inoculated solution to produce the starter culture:
  A. from 1 to 20 parts of dry culture medium consisting essentially of ingredients (a), (b) and (c) in amounts specified below on a 100 parts dry basis:
    a. from 0.5 to 10 parts of a nitrogen source selected from the group consisting of yeast extract, yeast autolysate, solubilized yeast and food yeast,
    b. from 1 to 30 parts of a citrate source selected from the group consisting of citric acid and salts of citric acid, amount of the citrate source being based on citrate anion exclusive of cation weight, and
    c. from 70 to 95 parts of a milk product to provide 100 parts of the culture medium on dry basis consisting essentially of a major amount of undecalcified sweet whey and a minor amount of undecalcified nonfat dry milk;
  B. from 80 to 99 parts of water; and
  C. an effective amount of a lactic acid producing bacteria to inoculate the solution of A and B to cause growth of the bacteria to flourish.

2. Process of claim 1 wherein the bacteria is selected from the group consisting of Streptococcus cremoris, Streptococcus lactis, Streptococcus citrovorus, Streptococcus paracitrovorus, Streptococcus thermophilus, Streptococcus durans, Streptococcus diacetilactis, Streptococcus faecalis, Lactobacillus acidophilus, Lactobacillus bulgaricus, Lactobacillus delbrueckii, Lactobacillus fermenti, Lactobacillus helveticus, Lactobacillus lactis, Latobacillus plantarum, Lactobacillus thermophilus, Leuconostoc mesenteroides, Propionibacterium species and mixtures thereof.

3. Process of claim 1 wherein from 0.1 to 5 parts of the starter culture are added per 100 parts of milk.

4. Process of claim 1 where from 0.5 to 1 part of the starter culture is added per 100 parts of milk.

5. Process of claim 1 wherein the citrate source is present in amount of from about 10 to about 20 parts.

6. Process or preparing a starter culture for cheese manufacture comprising the steps of inoculating an aqueous solution of a culture medium consisting essentially of 1 to 20 parts of dry culture medium and 80 to 99 parts of water, on 100 parts basis, with an effective amount of a lactic acid producing bacteria and incubating the inoculated solution to produce the starter culture, the culture medium consisting essentially of ingredients (a), (b), and (c) in amounts specified below on a 100 parts dry basis:
  a. from 0.5 to 10 parts of a nitrogen source selected from the group consisting of yeast extract, yeast autolysate, solubilized yeast, food yeast, amino acids, proteins and mixtures thereof;
  b. from 10 to 20 parts of a citrate source selected from the group consisting of ammonium citrate, sodium citrate, potassium citrate, citric acid and mixtures thereof, amount of the citrate source being based on citrate anion exclusive of cation weight, and
  c. a milk product being the remainder to provide 100 parts of the culture medium on dry basis which is a major amount of undecalcified sweet whey and a minor amount of undecalcified nonfat dry milk; the bacteria is selected from the group consisting of Streptococcus cremoris, Streptococcus lactis, Streptococcus citrovorus, Streptococcus paracitrovorus, Streptococcus thermophilus, Streptococcus durans, Streptococcus diacetilactis, Streptococcus faecalis, Lactobacillus acidophilus, Lactobacillus bulgaricus, Lactobacillus delbrueckii, Lactobacillus fermenti, Lactobacillus helveticus, Lactobacillus lactis, Lactobacillus plantarum, Lactobacillus thermophilus, Leuconostoc mesenteroides, Propionibacterium species and mixtures thereof and amount of the bacteria does not exceed 10 parts.

* * * * *